United States Patent [19]

Liau

[11] Patent Number: 4,861,725
[45] Date of Patent: Aug. 29, 1989

[54] MAMMALIAN CELL CULTURE APPARATUS

[76] Inventor: Ming Y. Liau, 4th Fl., No. 48, Lane 225, Chu Lin Rd., Yuang-Ho City, Taipie, Taiwan

[21] Appl. No.: 174,705

[22] Filed: Mar. 29, 1988

[51] Int. Cl.$^4$ .............................................. C12M 1/28
[52] U.S. Cl. ..................... 435/294; 435/296; 435/311; 435/288; 210/342
[58] Field of Search ............... 435/288, 296, 311, 294; 210/244, 323.1, 445, 342

[56] References Cited

U.S. PATENT DOCUMENTS

| | | | |
|---|---|---|---|
| 446,342 | 2/1891 | Goodacre | 210/342 |
| 3,580,840 | 5/1971 | Uridil | 435/311 X |
| 3,853,712 | 12/1974 | House et al. | 435/313 X |
| 4,201,845 | 5/1980 | Feder et al. | 435/285 |
| 4,242,461 | 12/1980 | Bartoli et al. | 435/288 |
| 4,603,109 | 7/1986 | Lillo | 435/41 |

FOREIGN PATENT DOCUMENTS

| | | | |
|---|---|---|---|
| WO86/02944 | 5/1986 | PCT Int'l Appl. | 435/311 |
| 430155 | 5/1974 | U.S.S.R. | 435/294 |
| 25582 | of 1903 | United Kingdom | 435/311 |
| 473224 | 10/1937 | United Kingdom | 210/342 |

Primary Examiner—Albert J. Makay
Assistant Examiner—Allen J. Flanigan
Attorney, Agent, or Firm—Birch, Stewart, Kolasch & Birch

[57] ABSTRACT

A cell culture apparatus includes a sealed container in which a plurality of porous tubular members are positioned. The tubular members are arranged concentrically. A removable sampling bar is inserted into the innermost tubular member in the container so that the sampling bar is positioned in proximity with the inner surface of the innermost tubular member.

11 Claims, 2 Drawing Sheets

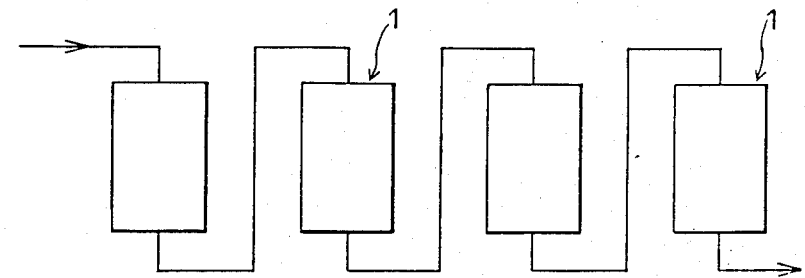
F I G. 3
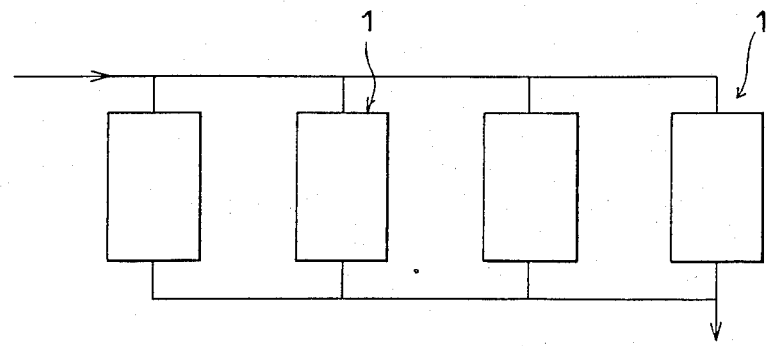
F I G. 4

MAMMALIAN CELL CULTURE APPARATUS

BACKGROUND OF THE INVENTION

The present invention relates to a mammalian cell culture apparatus which has a high ratio of surface area for growth to total apparatus volume and which can provide sufficient oxygen to high density cultures of mammalian cells grown in large volumes.

Anchorage-dependent cells have traditionally been grown on a large scale on the inside of rotating bottles. As the bottles roll, the cells are alternately exposed to oxygen in the air space and to the growth medium. The surface area for growth is only a small percentage of the total bottle volume, and thus many roller bottles are required to produce even small quantities of cells. For example, only $3 \times 10$ cells can be obtained from a bottle with a surface area of 500 cm. This low ratio of surface area for growth to total bottle volume results in high cost of serum usage. Furthermore, the roller bottles cannot provide sufficient oxygen to high density cultures of mammalian cells grown in large volumes.

SUMMARY OF THE INVENTION

It is therefore the main object of this invention to provide a cell culture apparatus which has a high ratio of surface area for growth to total apparatus volume.

Another object of this invention is to provide a mammalian cell culture apparatus which can provide sufficient oxygen to high density cultures of mammalian cells grown in large volumes by way of a perfusion method.

According to this invention, a mammalian cell culture apparatus includes a sealed container, a plurality of porous tubular members, and means for positioning the tubular members in the container in such a manner that the tubular members are arranged concentrically.

BRIEF DESCRIPTION OF THE DRAWINGS

Other features and advantages of this invention will become apparent from the following detailed description of a preferred embodiment of this invention with reference to the accompanying drawings in which:

FIG. 3 is a schematic view illustrating how four containers are connected in series; and FIG. 4 is a schematic view illustrating how four containers are connected in parallel.

DETAILED DESCRIPTION OF THE PREFERRED EMBODIMENT

Figure 1:
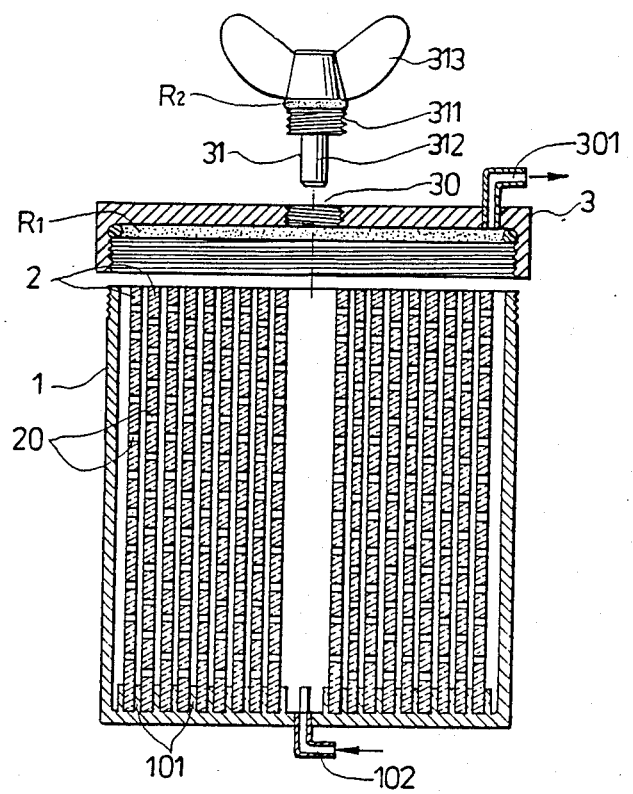
FIG. 1 is a partially exploded section of a mammalian cell culture apparatus according to this invention.
Figure 2:
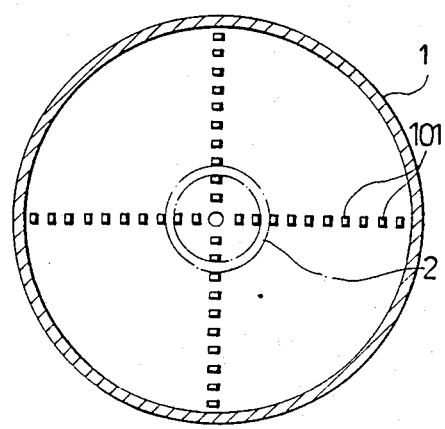
FIG. 2 is a sectional top view showing the container body of the mammalian cell culture apparatus.

Referring to FIGS. 1 and 2, there is shown a mammalian cell culture apparatus according to this invention. The apparatus includes a container body 1. Nine poruos tubular members 2 of different sizes are accommodated in the container body 1. The bottom wall of the container body 1 is formed with four rows of ten projections 101 extending upwardly from its upper surface in a criss-cross arrangement. The tubular members 2 are of the same wall thickness. Any adjacent pair of each row of projections 101 are spaced from each other at a distance slightly greater than the wall thickness of the tubular members 2 so that each of the tubular members 2 can be inserted tightly between adjacent projections 101, thereby positioning the tubular members 2 coaxially in the container body 1. Because each of the tubular members 2 has a number of closely spaced holes 20 (see FIG. 1), the culture medium will fill all the space in the container body 1. Thus, the apparatus will provide sufficient oxygen to high density cultures of mammalian cells grown in the container body 1 by way of a perfusion method.

A cover 2 is engaged threadably with the upper end of the container body 1. A first O ring R1 is disposed between the cover 3 and the container body 1 for establishing a liquid-tight seal therebetween.

The cover 3 has a threaded hole 30 formed through its center. A sampling bar 31 has an externally threaded middle portion 311 which engages with the threaded hole 30 in the cover 3. Connected to the lower end of the middle portion 311 is a diameter-reduced sampling portion 312 for being inserted into the innermost tubular member 2 in the container body 1. The sampling portion 312 is of a diameter slightly smaller than the inner diameter of the innermost tubular member 2 for convenience in sampling. To easily rotate the sampling bar 31, a butterfly-like actuator portion 313 is provided on the upper end of the middle portion 311. In addition, to establish a liquid-tight seal between the sampling bar 31 and the cover 3, a second O ring R2 is sleeved on the sampling bar 31 between the actuator portion 313 of the sampling bar 31 and the cover 3.

A charging tube 102 is passed through the bottom wall of the container body 1 so as to charge fresh media into the container body 1 therethrough. A discharging tube 301 is passed through the cover 3 so as to discharge media from the container body 1 therethrough. The culture space of the apparatus of this invention may be varied in accordance with the cell characteristics. If desired, some of the tubular members 2 may be removed from the container body 1 to increase the spaces between the tubular members 2. Or, the tubular members 2 may be thinned to increase the spaces between the tubular members 2. When the mammalian cells are too numerous to be cultivated in one container body 1, several container bodies 1 can be intercommunicated in series (see FIG. 3) or in parallel (see FIG. 4) by conduits. Various media are pumped into one of the conduits by a pump.

With this invention thus explained, it is apparent that various modifications can be made without departing from the scope and spirit of this invention. It is therefore intended that this invention be limited only as indicated in the appended claims.

I claim:

1. A cell culture apparatus, comprising:

a plurality of porous tubular members, a sealed container including said plurality of porous tubular members therein and having a sampling bar mounted removably thereon, said sealed container having a top wall through which a threaded hole is formed, said sampling bar having an externally threaded portion engaged with said threaded hole in said container, a diameter-reduced sampling portion connected to a lower end of said externally threaded portion for insertion into said container and into the innermost tubular member, a diameter-increased actuator portion connected to an upper end of said externally threaded portion, and an O ring sleeved on said sampling bar and clamped between said externally threaded portion of said sampling bar and said container for establishing a liquid-tight seal between said sampling bar and said container, said sampling portion of said sampling bar having a diameter slightly smaller than the inner diameter of said innermost tubular member, and means for positioning said tubular members in said container so that the tubular members are concentrically arranged.

2. The cell culture apparatus as claimed in claim 11, wherein said positioning means includes a row of projections, each of said projections projecting upwardly from a bottom wall of said container, each row of said projections being aligned in a radial direction so that each of said tubular members is inserted tightly between adjacent projections.

3. The cell culture apparatus as claimed in claim 1, wherein said tubular members are of different sizes.

4. A cell culture apparatus, comprising:
a plurality of porous tubular members,
a plurality of sealed containers intercommunicated with each other, each sealed container including said plurality of porous tubular members therein and having a sampling bar mounted removably thereon, each of said sealed containers having a top wall through which a threaded hole is formed, each of said sampling bars having an externally threaded portion engaged with said threaded hole in each of said containers, a diameter-reduced sampling portion connected to a lower end of said externally threaded portion for insertion into said container and into the innermost tubular member, a diameter increased actuator portion connected to an upper end of said externally threaded portion, and an O ring sleeved on said sampling bar and clamped between said externally threaded portion of said sampling bar and said container for establishing a liquid-light seal between said sampling bar and said container, said sampling portion of said sampling bar having a diameter slightly smaller than the inner diameter of said innermost tubular member, and means for positioning said tubular members in each of said containers so that the tubular members are concentrically arranged.

5. The cell culture apparatus as claimed in claim 4, wherein said containers are connected in series.

6. The cell culture apparatus as claimed in claim 4, wherein said containers are connected in parallel.

7. The cell culture apparatus as claimed in claim 4, wherein each of said positioning means includes two rows of projections, each of said projections projecting upwardly from a bottom wall of said container, each row of said projections being aligned in a radial direction so that each of said tubular members is inserted tightly between adjacent projections.

8. The cell culture apparatus as claimed in claim 4, wherein said tubular members are of different sizes.

9. The cell culture apparatus as claimed in claim 3, wherein a first tube is positioned through a bottom portion of the container and a second tube is positioned in an upper portion of the container for charging media into the container.

10. The cell culture apparatus as claimed in claim 9, wherein the first tube is a charging tube and the second tube is a discharging tube.

11. The cell culture apparatus as claimed in claim 9, wherein said bottom portion of the container is a bottom wall and said upper portion of the container is the cover of the container.

* * * * *